United States Patent
Buettner-Janz

(10) Patent No.: US 8,888,851 B2
(45) Date of Patent: Nov. 18, 2014

(54) INTERVERTEBRAL DISC PROSTHESIS WITH TRANSVERSALLY ARCHED, CURVED CYLINDRICAL ARTICULATION SURFACES FOR THE LUMBAR AND CERVICAL SPINE

(76) Inventor: Karin Buettner-Janz, Berlin (DE)

( * ) Notice: Subject to any disclaimer, the term of this patent is extended or adjusted under 35 U.S.C. 154(b) by 432 days.

(21) Appl. No.: 13/209,488

(22) Filed: Aug. 15, 2011

(65) Prior Publication Data

US 2012/0089230 A1    Apr. 12, 2012

Related U.S. Application Data

(60) Division of application No. 11/379,091, filed on Apr. 18, 2006, now Pat. No. 8,016,888, which is a continuation-in-part of application No. PCT/DE2005/001886, filed on Oct. 18, 2005.

(30) Foreign Application Priority Data

Oct. 18, 2004 (WO) ................. PCT/DE2004/002333

(51) Int. Cl.
  A61F 2/44    (2006.01)
  A61F 2/30    (2006.01)
  A61F 2/46    (2006.01)

(52) U.S. Cl.
  CPC ..... *A61F 2/4425* (2013.01); *A61F 2310/00544* (2013.01); *A61F 2002/30841* (2013.01); *A61F 2310/00449* (2013.01); *A61F 2230/0069* (2013.01); *A61F 2002/304* (2013.01); *A61F 2220/0025* (2013.01); *A61F 2002/30004* (2013.01); *A61F 2002/3069* (2013.01); *A61F 2002/30392* (2013.01); *A61F 2250/0014* (2013.01); *A61F 2002/30232* (2013.01); *A61F 2002/3008* (2013.01); *A61F 2310/00748* (2013.01); *A61F 2002/302* (2013.01); *A61F 2230/0065* (2013.01); *A61F 2/4611* (2013.01); *A61F 2250/0098* (2013.01); *A61F 2310/00407* (2013.01); *A61F 2002/30224* (2013.01); *A61F 2002/30685* (2013.01); *A61F 2002/443* (2013.01); *A61F 2002/30397* (2013.01)
USPC ........................................ 623/17.14; 623/17.15

(58) Field of Classification Search
  USPC ............................................. 623/17.11–17.16
  See application file for complete search history.

(56) References Cited

U.S. PATENT DOCUMENTS

| 5,258,031 | A | 11/1993 | Salib et al. |
| 5,401,269 | A | 3/1995 | Buettner-Janz et al. |

(Continued)

FOREIGN PATENT DOCUMENTS

| CA | 2376097 A1 | 12/2000 |
| DE | 3529761 C2 | 6/1994 |

(Continued)

OTHER PUBLICATIONS

Bomley, Anna, "Spinal Devices: Market Opportunities and Technology Trends," in Clinical Reports, CBS925, PJB Publications, Ltd, Jun. 2004, Surrey, UK.

*Primary Examiner* — Jan Christopher Merene
(74) *Attorney, Agent, or Firm* — Joyce von Natzmer; Agris & von Natzmer LLP

(57) ABSTRACT

An intervertebral disc prosthesis for the total replacement of an intervertebral disc within the lumbar and cervical spine is disclosed. The intervertebral disc prosthesis comprises articulating sliding partners, wherein the upper sliding partner is adapted for a firm assembly to an upper vertebral body and the lower sliding partner is adapted for a firm assembly to a lower vertebral body. The functional two part design provides a dorsoventral motion and in the transversal plane a rotational motion around a fictitious vertical axis as a result of a laterolaterally aimed, transversally arched, ventrally curved cylindrical convexity and corresponding concavity but prevents an inclination of the sliding partners in a lateral direction. According to the invention, the intervertebral disk prostheses are suited for implantation from lateral and ventrolateral, particularly in revision surgeries.

33 Claims, 6 Drawing Sheets

(56) References Cited

U.S. PATENT DOCUMENTS

| | | | |
|---|---|---|---|
| 5,593,409 A | 1/1997 | Michelson | |
| 5,888,226 A | 3/1999 | Rogozinski | |
| 6,019,792 A | 2/2000 | Cauthen | |
| 6,179,874 B1 | 1/2001 | Cauthen | |
| 6,402,785 B1 * | 6/2002 | Zdeblick et al. | 623/17.16 |
| 6,610,093 B1 | 8/2003 | Pisharodi | |
| 7,001,433 B2 | 2/2006 | Songer et al. | |
| 7,083,649 B2 | 8/2006 | Zucherman et al. | |
| 7,156,876 B2 | 1/2007 | Moumene et al. | |
| 7,270,682 B2 | 9/2007 | Frigg et al. | |
| 2003/0069586 A1 | 4/2003 | Errico et al. | |
| 2003/0074069 A1 | 4/2003 | Errico et al. | |
| 2003/0139813 A1 | 7/2003 | Messerli et al. | |
| 2003/0191534 A1 | 10/2003 | Viart et al. | |
| 2003/0208273 A1 | 11/2003 | Eisermann et al. | |
| 2004/0024461 A1 | 2/2004 | Ferree | |
| 2004/0030390 A1 | 2/2004 | Ferree | |
| 2004/0073310 A1 | 4/2004 | Moumene et al. | |
| 2004/0117021 A1 | 6/2004 | Biedermann et al. | |
| 2004/0143332 A1 | 7/2004 | Krueger et al. | |
| 2004/0199253 A1 | 10/2004 | Link et al. | |
| 2004/0243240 A1 | 12/2004 | Beaurain et al. | |
| 2005/0261772 A1 | 11/2005 | Filippi et al. | |
| 2006/0235527 A1 | 10/2006 | Buettner-Janz et al. | |
| 2006/0235528 A1 | 10/2006 | Buettner-Janz | |
| 2006/0241772 A1 | 10/2006 | Buettner-Janz et al. | |
| 2010/0234954 A1 * | 9/2010 | Justis et al. | 623/17.12 |

FOREIGN PATENT DOCUMENTS

| | | |
|---|---|---|
| DE | 10242329 A1 | 4/2004 |
| DE | 20320454 U1 | 10/2004 |
| DE | 2004002333 | 7/2005 |
| DE | 2005001886 | 3/2006 |
| EP | 0560141 B1 | 10/1996 |
| EP | 1039855 B1 | 10/2000 |
| WO | 2004041131 A2 | 5/2004 |

* cited by examiner ined prosthesis replaces this by just one piece, namely the polyethylene core, which allows the axial rotation. With respect to the axial load this only happens within the convex-concave construction of the articulation, which corresponds to the natural conditions. The tight guidance of the CHARITÉ prosthesis in the frontal plane is missing in the invented prosthesis, which does not play a role in the lumbar and cervical spine with its natural, great mobility in the frontal plane.

INTERVERTEBRAL DISC PROSTHESIS WITH TRANSVERSALLY ARCHED, CURVED CYLINDRICAL ARTICULATION SURFACES FOR THE LUMBAR AND CERVICAL SPINE

CROSS REFERENCE SECTION

This is a divisional application of U.S. application Ser. No. 11/379,091, filed Apr. 18, 2006, now U.S. Pat. No. 8,016,888 and which is a continuation-in-part application of international application no. PCT/DE2005/001886, filed Oct. 18, 2005 designating the U.S. and claiming priority from international application no. PCT/DE2004/002333, filed Oct. 18, 2004. Both of these applications are incorporated herein in their entirety by reference.

FIELD OF THE INVENTION

The invention relates to an intervertebral disc prosthesis for the total replacement of an intervertebral disc of the lumbar and cervical spine.

BACKGROUND OF THE INVENTION

The idea of function-retaining artificial replacements for intervertebral discs is younger than that for replacements of artificial joints of extremities, but nonetheless about 50 years old [Büttner-Janz, Hochschuler, McAfee (Eds.): The Artificial Disc. Springer Verlag, Berlin, Heidelberg, N.Y. 2003]. It results from biomechanical considerations, unsatisfactory results of fusion surgeries, disorders adjacent to fusion segments and the development of new materials with greater longevity.

The publications and other materials, including patents, used herein to illustrate the invention and, in particular, to provide additional details respecting the practice are incorporated herein by reference.

By means of function-retaining disc implants, it is possible to avoid fusion surgery, i.e. to maintain, or to restore the mobility within the intervertebral disc space. In an in-vitro experiment it is also possible to achieve a normalization of the biomechanical properties of the motion segment to a large extent through the implantation of an artificial intervertebral disc after a nucleotomy.

Implants for the replacement of the whole intervertebral disc differ from those for the replacement of the nucleus pulposus. Accordingly, implants for the total replacement of the intervertebral disc are voluminous; they are implanted via a ventral approach. An implantation of a prosthesis for total replacement of the intervertebral disc immediately after a standard nucleotomy can therefore not be carried out.

The indication for a function-retaining intervertebral disc replacement as an alternative to the surgical fusion includes, besides the painful discopathy, also pre-operated patients with a so-called post discectomy syndrome, patients with a recurrent herniated intervertebral disc within the same segment and patients having a pathology within the neighboring intervertebral disc as a consequence fusion surgery.

Presently, a total of more than 10 different prostheses are clinically used for the total replacement of intervertebral discs. For the lumbar spine the, CHARITÉ Artificial Disc, the PRODISC, the MAVERICK, the FLEXICORE and the MOBIDISC (Overview in Clinical Reports, PJB Publications Ltd., June 2004) are particularly well known, and for the cervical spine the BRYAN prosthesis, the PRESTIGE LP prosthesis, the PRODISC-C and the PCM prosthesis, which will be described below.

The PRODISC prosthesis for the lumbar spine is being implanted since 1999, following its further development to the PRODISC II. The PRODISC prosthesis has been in use as a lumbar spine implant since 1999, until it was replaced by the further developed PRODISC II. Although with respect to its components (a three-part intervertebral disc prosthesis), it is functionally a two-part prosthesis with its sliding partners made of metal and polyethylene. Implantations of the PRODISC are carried out in the lumbar spine and with an adapted model of the prosthesis, the PRODISC-C, also in the cervical spine. Different sizes, heights (achieved by the polyethylene core) and angles of lordosis (achieved by the metal endplates) are available. Bending forward and backward as well as to the right and to the left is possible to the same extent of motion; the axial rotation is not limited in the construction.

The same applies to both two-part prostheses for the cervical spine, the PCM prosthesis with its sliding partners metal and polyethylene and the PRESTIGE LP prosthesis with its sliding partners metal. As special feature of the construction of the PRESTIGE LP prosthesis it has the possibility for an anterior-posterior translation, due to the horizontal ventrally prolonged concavity, which, in a frontal section, has the same radius as the convexity.

The MAVERICK and the FLEXICORE for the lumbar spine are functionally a two-part prostheses with spherical convex-concave sliding partners, both with sliding partners made of metal. In contrast, the MOBIDISC is functionally a three-part prosthesis with sliding partners of metal-polyethylene and two articulation surfaces. One area is a segment of a sphere, as it is in the three afore mentioned prostheses, with a convex and a concave surface of the articulating partners each of the same radius, the other area of the MOBIDISC being plane. Although a limitation of the axial rotation is planned within the plane section, it is not limited within the convex-concave area of articulation. In contrast the FLEXICORE has a small stopping area within the spherical sliding surfaces limiting the rotation movement.

The BRYAN prosthesis is clinically used as a compact prosthesis for total replacement of intervertebral discs of the cervical spine. It is attached to the vertebral bodies by convex titanium plates with a porous surface and achieves its biomechanical properties by virtue of a polyurethane nucleus.

The longest experience exists with the CHARITÉ prosthesis, which is the subject matter of DE 35 29 761 C2 and U.S. Pat. No. 5,401,269. This prosthesis was developed in 1982 by Dr. Schellnack and Dr. Büttner-Janz at the Charité in Berlin and was later on named SB CHARITÉ prosthesis. In 1984 the first surgery took place. The intervertebral disc prosthesis was further developed into model III and has been implanted over 10,000 times worldwide (DE 35 29 761 C2, U.S. Pat. No. 5,401,269) since 1987 and is still being used. The prosthesis is functionally a three-parted being with the sliding partners being metal and polyethylene with two identical spherical sliding surfaces. It has a transversally mobile polyethylene core and the accordingly adapted concave cups within two metal endplates. For the adaptation to the intervertebral space, the CHARITÉ prosthesis provides different sizes of metal plates and different heights of size adapted sliding cores as well as angled prosthetic endplates, which when implanted vice versa in sagittal direction can also be used as replacement for the vertebral body. The primary fixation of the CHARITÉ prosthesis is achieved by six teeth, which are located in groups of three slightly towards the middle next to the frontal and rear edge of each prosthetic plate.

The other prosthesis have other primary fixations on their surfaces directed towards the intervertebral bodies, e.g. a sagitally running keel, a structured surface, a convex shape with for instance crosswise running grooves and combinations thereof, also with differently located teeth. Furthermore screw fixations can be used, either from ventral or from within the intervertebral space into the intervertebral body.

To assure a long-term fixation of the prosthetic endplates to the intervertebral bodies and to thus generate a firm connection with the bone, a surface was created in similitude to cement-free hip and knee prostheses, which combines chrome-cobalt, titanium and calcium phosphate in such a way that it is possible for bone to grow directly onto the endplates. This direct connection between prosthesis and bone, without the development of connective tissue, makes a long-term fixation of the artificial intervertebral disc possible and reduces the danger of loosening or displacements of the prosthesis and material breakage.

One primary objective of function retaining intervertebral disc replacements is to closely adapt the motions of the prosthesis to the ones of a healthy intervertebral disc. Directly connected to this is the motion and stress for the facet joints, which following inappropriate biomechanical stress have their own potential for disorders. There can be abrasion of the facet joints (arthritis, spondylarthritis), a formation of osteophytes. As result of these osteophytes and also by a pathologic course of motion of the intervertebral disc alone, the irritation of neural structures is possible.

The healthy intervertebral disc is, in its interactions with other elements of the motion segment, composed in such a way that it allows for limited motion. For example, within the intervertebral disc, motions to the front and back are combined with rotary motions, and side motions are also combined with other motions. The motion amplitudes of a healthy intervertebral disc are very different, with respect to the extension (bending back) and flexion (bending forward) as well as to the lateral bending (right and left) and rotary motion. Although of common basic characteristics, there are differences between the motion amplitudes of the lumbar and cervical spine.

During motion of the intervertebral disc the centre of rotation changes, i.e. the motion of the intervertebral disc does not take place around a fixed center. Due to a simultaneous translation movement of the adjacent vertebrae, the center changes its position constantly (inconstant center of rotation). The prosthesis according to DE 35 29 761 C2 shows a construction which differs relative to other available types of prostheses which are build like a ball and socket joint and as a result move around a defined localized centre of rotation. By virtue of the three-part assembly of the prosthesis according to DE 35 29 761 C2, with two metallic endplates and the interpositioned freely mobile polyethylene sliding core, the course of motion of a healthy intervertebral disc of the human spine is mimicked as far as possible, however without the exact motion amplitudes in the specific motion directions.

A further important feature of the healthy lumbar intervertebral disc is its trapezium shape, which is primarily responsible for the lordosis of the lumbar and cervical spine. The vertebral bodies themselves contribute only to a minor extent to the lordosis. During prosthetic replacement of intervertebral discs the lordosis should be maintained or reconstructed. The CHARITÉ disc prosthesis provides four differently angled endplates, which moreover can be combined with each other. However, this surgery requires more surgical effort and has the risk of damaging the vertebral endplates which is associated with a danger of subsidence of the prosthesis into the vertebral bodies. Additionally, if the adjustment of the lordosis is poor and an optimal load of the center of the polyethylene core was not achieved, the prosthesis has to be removed completely.

To avoid sliding or a slip-out of the middle sliding partner from the endplates, DE 35 29 761 C2 discloses a sliding core with a two-sided partly spherical surface (lenticular), with a plane leading edge and at the exterior with a ring bulge, which will lock between the form-adapted endplates during extreme motion. DE 102 42 329 A1 discloses a similar intervertebral disc prosthesis which has a groove around the contact surfaces, in which an elastic ring is embedded that is in contact with the opposite contact area for better guidance.

EP 0 560 141 B1 describes a three-part intervertebral disc prosthesis, which also comprises two endplates and an interpositioned prosthetic core. The intervertebral disc prosthesis, described in this document, provides resistance during rotation of its endplates in opposing directions around a vertical rotary axis without a contact between the prosthetic endplates. This is achieved by a soft limitation of the endplates during rotation onto the prosthesis core caused by the weight, which acts on the plates as a result of the biomechanical load transfer within the spine, because the corresponding radii of curvature differ in a median-sagittal and frontal transection.

The above mentioned models are permanently anchored in the intervertebral spaces as implants. Especially due to a load transfer over too small surface areas, a migration of the endplates into the vertebral bodies and thus a dislocation of the complete implant is possible in middle to long-term use, resulting in artificial stress for the vertebral bodies and the adjacent nerves and in the end for the total motion segment, and leading to new complaints of the patients. The longevity of the polyethylene also needs to be discussed because destruction of the sliding cores has been observed, which necessitated revision surgery, so far in the form of a fusion of the motion segment The risk of postoperatively persisting complaints is higher if the facet joints of the surgical segment already show signs of arthritis at prosthetic implantation. It also has to be taken into account that a too large segmental range of motion, resulting from the design of the prosthesis, may potentially lead to new complaints for the patient. This is most likely caused by an overloading or malapropos stress on the facet joints, which may lead to painful arthritis. The same applies to prosthesis that have been implanted frontally inclined or that have postoperatively developed a malapropos positioning. Furthermore, fusion surgery leads to an increased strain on the neighboring segments with the danger of a later indication for surgery at this level. An intervertebral disc prosthesis with a segmental partial function may thus present a solution to this problem.

EP 1 039 855 B1 discloses a partially cylindrical implant for the intervertebral space. This implant has an elastic core, which is located between two end plates that are assembled to an upper and a lower vertebral body. Motion within the intervertebral space is only possible as far as the elastic core can be compressed.

U.S. Pat. No. 5,539,409 also discloses a partially cylindrical implant for the intervertebral space. Such as implant has a rough surface and, as per the invention, is to be filled with substances that will encourage the fusion of the implant with the bone of the neighboring vertebra. A motion of the affected segment of the spine after implantation is therefore not possible.

Furthermore, intervertebral disc prostheses, from the state of the art known, have one or more cylindrical compressible middle parts. An example can be found in CA 2 376 097 A1, which discloses a prosthesis comprising a cylindrical upper and lower hull, in between which a cylindrical middle part made of an elastic material is positioned.

In the intervertebral disc prostheses with a cylindrical core, known from the state of the art, this is mostly made of an elastic material or is firmly assembled to the neighboring vertebral body. U.S. Pat. No. 5,258,031 discloses a lateral section, partially cylindrical, articulation area of a two-part intervertebral disc prosthesis, which permits a bending to the sides via the lateral edges of the cylindrical marginal convexity, so that the load bearing on the endplates is partially only on the edges and so that an increased wear of these regions of the articulation areas is to be expected. Such a prosthesis can only be implanted by ventral surgery because of the size of the keels and/or the fixation of the prosthesis is by means of screwing.

There is a need for an intervertebral disc prosthesis for the total replacement of the intervertebral disc, which will enable a dorsoventral and a rotational motion of a spinal segment, but does not allow for sideways bending. It will be possible to implant the prosthesis by surgery from ventrolateral and lateral as well.

This need is addressed by the present invention. The invention comprises an intervertebral disc prosthesis, namely a functionally two-part prosthesis.

SUMMARY OF THE INVENTION

The functional two-part prosthesis is characterized by
a) a first sliding partner having at a side opposite of the side for assembly with a vertebral body a convexity and the convexity correlates to a segment of a cylinder along its longitudinal axis from right to left lateral with a transversal ventrally directed arched curvature, wherein the convexity is surrounded dorsally, ventrally and to both lateral sides by an edge, and
b) a second sliding partner having at a side opposite of the side for assembly with a vertebral body concavity and the concavity corresponds to the convexity of the first sliding partner, wherein the concavity is surrounded dorsally, ventrally and to both lateral sides by an edge, and
c) the edges of both sliding partners have an outwardly opening aperture angle towards each other, wherein no inclination of the sliding partners towards each other is possible in a lateral direction and the maximally possible motion of the sliding partners in dorsoventral direction is limited by a gap-closure of the edges of the two sliding partners, and
d) the rotation of the sliding partners towards each other is limited by a tolerance between convexity and concavity right and left laterally of the transversally curved cylindrical articulation areas.

The prosthesis comprises articulating sliding partners wherein an upper sliding partner is firmly assembled to an upper vertebral body and a lower sliding partner is firmly assembled to a lower vertebral body and the sliding partners form an interdigitating articulation area on their inner surfaces that are directed towards each other.

The arched curvature of the cylindrical convexity and the corresponding concavity is only intended to a small degree. By virtue of the ventrally arched curvature of the articulation area of the prosthesis another partial function of the natural intervertebral disc, besides the motion in ventral and dorsal direction, is realized, namely rotation. The facet joints in the human body are approximately located on the sector or circularly parallel to it, which is partially formed by the arched curvature of the articulation areas with a particularly advantageous biomechanical influence on the facet joints during rotation. The rotation of the sliding partners towards each other results in less strain and maintains the boundary between the bone and the implant while preserving the prosthesis material.

As per the invention, it is intended that the ventral and dorsal radii of curvature of the cylindrical convexity and the corresponding concavity run towards each other with a constant distance in the transversal overview, because the ventral and dorsal curvature is derived from two circles with different radii but identical midpoints. As per the invention, it is, however, also intended that the segmental arches do not run towards each other with a constant distance and that they either run towards each other in lateral direction or that they have an increasing distance between them laterally. In the first case, the convexity and corresponding concavity would taper off laterally so that more "play" arises for a combined rotation and inclination motion. In the second case the contact area of the convexity with the concavity would be larger, which would result in an improved durability of the material of the articulation areas.

In essence, the maximal possible motion of the sliding partners of an intervertebral disc prosthesis, as per the invention, is limited by
a) the radius of curvature as well as the height of the convexity and a height of the concavity and of the respective edges surrounding an articulation area ventrally and dorsally, and
b) the aperture angle between the edges of the neighboring sliding partners, which is formed by the edges running at an incline and/or horizontally and a gap-closure during terminal contact of the edges of neighboring sliding partners, and
c) the tolerances between convexity and concavity to the right and left laterally end, respectively, and the extent of curvature of the cylindrical articulation area at rotation of the sliding partners with respect to a fictitious vertical axis.

The two-part prosthesis is particularly advantageous in cases of implantations in multiple adjacent intervertebral spaces because of the model-immanent stability. It is also advantageous for intervertebral spaces that are inclined to the left or right and which are to be corrected. Furthermore, the two part prosthesis can be implanted in patients, where the implantation is to be carried out from a lateral or ventrolateral approach, e.g. via a trans-psoas approach. Such an indication would, for instance, be given in patients who have previously had surgery to the spine from a ventral approach, who require a change of prostheses after primary implantation of a prosthesis from a ventral approach, because the scarring of the large blood vessels in the ventral region of the spine presents a considerably increased surgical risk in cases of a ventral re-operation. With a lateral approach the annulus fibrosus can be incised generously on one side, so that an optimal prosthesis with respect to the area for the purpose of a load transfer over a large area, can be positioned, without a postoperatively arising frontal segmental inclination, as a result of the one-sided lateral liberation of the intervertebral disc. It is further feasible that patients, who have arthritis of the facet joints without osteophytes, can be treated, because postoperatively bending motions to both lateral sides do not stresses these joints.

Because of the narrow anatomical space, the two-part prosthesis is more suited for the cervical spine.

With respect to the present invention the three body axes are described by the following terms: A "sagittal section" or a view in the "sagittal plane" enables a lateral view, because the section plane runs vertically from the front to the back. The term "front" is synonymous "ventral" and the term "back" to "dorsal", because using these terms, the orientation of the prosthesis within the body is indicated. A "frontal section" or the "frontal plane" is a vertical cross-section from one side to the other. The term "lateral" stands for sidewise. Sagittal and frontal sections are vertical sections as they both run in a vertical plane, but 90 degree displaced from one another. A view in the "transversal plane" or a "transversal section" shows a top-view onto the prosthesis, because it is a horizontal section.

With respect to the description and depiction of the present invention, an articulation area signifies that region of the sliding partners, which comprises the curved convex and concave parts of the surfaces, which come into contact or articulate with each other. Because of this the articulation area is synonymous with the term sliding area.

The term "corresponding," with respect to the articulating sliding surfaces designates not only congruent convex and concave shaped surfaces articulating with each other. Moreover this term also designates articulating surfaces that are not completely congruent. Such "deviations" or tolerances regarding the sliding surfaces of articulating sliding partners can be caused by the chosen materials and shapes. Alternatively, the convexity and the concavity may intentionally be not completely congruent, for instance in order to specifically assign the desired range of motion of the articulating partners.

Besides the advantages resulting from the shape of the arched, curved convex-concave parts of the articulation surfaces, as per the invention, the intervertebral disc prostheses have further advantages. The concavities of upper and lower sliding partner of a two-part intervertebral disc prosthesis are each enclosed by an edge.

An edge, as per the invention, indicates an area located between outer rim of the respective sliding partner and convexity or concavity. The edges of the respective sliding partners run horizontally and/or obliquely and preferably have a plane surface. It is essential for the design of the surfaces of the edges, that during terminal inclination of the sliding partners towards each other a maximally possible contact between the edges of the sliding partners is guaranteed. Should the edges not have a plane surface, they have to in any case be designed in such a way that when they close towards each other, a maximally possible contact arises between them. The height of the edges at the articulation area and the area of the edge along the ventral or dorsal articulation area is equally or differently designed, however the marginal height may vary in such a way from ventral to dorsal that the motion possibility is purposefully larger to the ventral than to the dorsal direction.

The edges of convexity and concavity always have, without incline of the sliding partners towards each other, an outward opening angle (aperture angle) in every sagittal section plane. During terminal inclination of the sliding partners towards each other anteriorly and posteriorly, it comes to a gap-closure between the edges of the articulation areas. The maximal inclination angles are limited by contact of the transition area between convex and concave articulation areas. Although this contact is limiting for the further motion of the sliding partners towards each other, it is not the only area outside the concave-convex articulation areas, which comes into contact at terminal inclination. The edges of the sliding partners up unto their peripheral rim are designed in such a way, that these also participate in the gap-closure.

By this measure, as per the invention, the load bearing surface area is increased at terminal inclination of the prosthesis, during which an inclination of the prosthesis up until its limitation takes place. The areas in contact are further protected against wear because the pressure is taken up by a plane surface and not by small contact areas, resulting in a more durable prosthesis.

As per the invention, it is further intended that a cylindrical convexity has one-sidedly conically diminishing radii along its longitudinal axis. In such a model, the edge has according adaptations so that the ventrodorsal and rotation motions are still possible. By virtue of this "leaning" cylinder it is possible to make adaptations to maladjustment of the intervertebral space and/or to sustain or balance an existing scoliosis, where it is indicated.

Regarding the material of the prosthesis, as per the invention, it is intended, that the sliding partners are built as a single piece or at least one sliding partner comprises at least two permanently or firmly, but reversibly attached parts, whereas the convexity and/or the concavity is the part that is permanently or firmly, but reversibly assembled to the corresponding sliding partner, or the convexity and/or concavity have suitable means for a permanent or firm, but reversible assembly, wherein parts connected with each other comprise the same material or different materials or the surfaces of the parts are coated equally or differently. As suitable means for the assembly, adaptations of the shape of the parts to be connected, as per the invention, are intended, such as flat broadenings which are part of the edge or which form the whole edge, or recesses.

As far as an intervertebral disc prosthesis comprises permanent or firmly, but reversibly attached parts, it is intended that the assembly is achieved by a tongue and groove assembly, a track and corresponding recess, a snap mechanism, gluing or screwing.

The sliding partners are manufactured from well established materials in implantation techniques; for instance upper and lower sliding partner are made of rust free metal with a firm, but reversible assembled part of medicinal polyethylene. Other combinations of materials are also possible. The use of other alloplastic materials, which may also be bio-active, is also intended. The sliding partners have a high gloss polish at their contact areas to minimize abrasion (low-friction principle). Furthermore, a coating of the particular sliding partners with appropriate materials is also planned. Favored materials are: titanium, titanium alloys, titanium carbide, alloys of cobalt and chrome or other appropriate metals, tantalum or appropriate tantalum alloys, suitable ceramic materials as well as suitable plastics or compound materials.

For a two-part intervertebral disc prosthesis, as per the invention, a maximal aperture angle of 6°-10° including, for example 6°-7°, 6°-8°, 6°-9°, 7°-8°, 7°-9°, 7°-10°, 8°-9° or 8°-10° during one-sided gap closure of the sliding partners during extension or flexion is intended. The concrete maximal motions can be constructively adapted for the lumbar and cervical spine, without the need of an "individual prosthesis" for every single intervertebral disc. The dorsal and ventral aperture angles correspond to the natural segmental mobility and are reached by suitable choices of convexities and concavities in connection with the design of the surrounding edges. That way a ventrally larger inclination of the sliding partners towards each other than dorsally is enabled, which correlates to the physiological situation of the lumbar spine. To compensate for the tolerances within the motion segment an additional 3° will be included for every direction of motion.

For a functional two part-part intervertebral disc prosthesis, as per the invention, a transversal ventrally directed arched, cylindrical convexity and concavity of articulating sliding partners enables as well as limits a rotation around a fictitious vertical axis. By virtue of this model, as per the invention, a rotation of the sliding partners towards each other is enabled, which depending on the extent of the arched curvature allows a rotation around a fictitious central vertical axis of up to 3 degrees, including up to about 2 degrees or up to about 1 degree, for the lumbar spine and up to 6 degrees, including up to about 5 degrees, up to about 4 degrees, up to about 3 degrees, up to about 2 degrees or up to about 1 degree, for the cervical spine to each side. To compensate for the tolerances within the motion segment an additional 2 degrees to each side is included.

In a further preferred design of a two-part intervertebral disc prosthesis, as per the invention, a shift of up to 4 mm, including up to about 3 mm, up to about 2 mm or up to about 1 mm, away from a midline sagittal section to dorsal of the convexity and corresponding concavity is intended.

Particularly, a dorsally displaced center of rotation corresponds above all to the physiological situation between the lumbar spine and the sacral bone and at same time the differences between the possible inclination angles in extension and flexion are achieved.

It is furthermore intended that the edges of the sliding partners end outwardly rectangular, otherwise angular, curved or combined straight, curved and/or angular. The articulating concavity has a shape corresponding to the lateral shape of the convexity.

Further, it is intended for an intervertebral disc prosthesis, as per the invention, that the outer circumferences of the upper and lower sliding partner may taper off from dorsal to ventral (lumbar spine) or from ventral to dorsal (cervical spine) in a transversal view. This tapering off of the outer circumferences of the upper and lower sliding partner may laterally be in the form of identical curves and is preferably a segment of a circle. Where necessary, area and shape of the outer circumference of the upper and lower sliding partner can be equal or unequal and thus adapted to the size of the respective vertebral body to which they are assembled.

The tapering off shape of the upper and lower sliding partner generally corresponds to the prosthetic plates usable area of a vertebral body in a transversal view and thus leads to an optimal utilisation of the available area of a vertebral body for the anchoring of the sliding partners, with the objective of a load transfer onto as large as possible a surface area of the load bearing on the sliding partners.

Adaptations to the sliding partners, as per the invention, of the intervertebral disc prosthesis are further intended, in which upper and/or lower sliding partner are built in such a way in a frontal and/or sagittal section, that the out- and inside of the upper and/or lower sliding partner are parallel or not parallel to each other. By this measure, as per the invention, an intervertebral disc prosthesis, as per the invention, can be adapted to vertebral body endplates, which are not standing parallel in a frontal view or which, in a sagittal view, should build an optimal lordosis and positioning of the sliding areas.

It is further intended, that in a two-part design, as per the invention, the convexity is parallel or nonparallel with respect to a fictitious horizontal. The convexity and corresponding concavity in the two-part prosthesis is symmetrical or asymmetrical in its surface design. By virtue of the angular convexity, adaptations to asymmetries of the intervertebral space, into which the prosthesis is to be implanted, are also possible.

In a preferred model, the transversal ventrally running arched curvature of the convexities each differ from the middle to lateral side. The concavities of the articulation sliding partners have correspondingly arched curvatures. In this case of a ventrally asymmetrically running arched curvature, alternative an interruption of the convexity is centrally intended, with in this case the respectively corresponding concavity being able to have an interruption in form of a bridge.

The different arched curvatures offer the advantage that adaptations to the different positions of the facet joints can be made. This enables an optimal integration of the position of the facets of the facet joints within the asymmetrically, ventrally arched convexities during rotation.

For a reliable anchorage of the implants within the intervertebral space, a marginal and/or plane interdigitation of the exterior sides of the upper and lower sliding partner serves for the connection with an upper and lower vertebral body. The exterior sides themselves are flat or convex in shape and it is possible to coat the interdigitation or the vertebra-directed surfaces with or without interdigitation bio-actively or blunt. To minimize the risk of fracturing the vertebral body, a fixation with three ventrally arranged and two dorsally placed anchoring teeth is preferred. As an alternative, laterally continuously arranged rows of teeth from front and back or obliquely running rows of teeth are favoured for the implantation of the prosthesis from lateral and ventrolateral approaches and for an improved guidance of the upper and lower sliding partner during implantation between the vertebral bodies, because the forceps of the surgeon can grip in the middle gap between the rows of teeth or into holes of the upper and lower sliding partner at the level with the teeth.

To facilitate implantation or explantation of the intervertebral disc prosthesis, the upper and/or lower sliding partner are furbished with a provision for instruments in a further design. These provisions preferably comprise holes or moulds, into which the required instrument of the surgeon can grip so that a secure fixation of the respective sliding partner is possible.

Furthermore, as absolute measurements for an intervertebral disc prosthesis, as per the invention, a maximal breadth (frontal view) of 14 to 48 mm, including about 16 mm, about 18 mm, about 20 mm, about 22 mm, about 24 mm, about 26 mm, about 28 mm, about 30 mm, about 32 mm, about 34 mm, about 36 mm, about 38 mm, about 40 mm, about 42 mm, about 44 mm or about 46 mm, a maximal depth (sagittal view) of 11 to 35 mm, including about 13, about 15 mm, about 17 mm, about 19 mm, about 21 mm, about 23 mm, about 25 mm, about 27 mm, about 29 mm, about 31 mm, about 33 mm, and a maximal height of 4 to 18 mm including about 6 mm, about 8 mm, about 10 mm, about 12 mm, about 14 mm or about 16 mm, are intended. These measurements are taken from the natural conditions of the lumbar and cervical spine and assure that the situation with an intervertebral disc prosthesis, as per the invention, comes very close to the in vivo situation.

Further, for an intervertebral disc prosthesis as per the invention one or more X-ray contrast giving markers are provided which are located under the surface of each of the non X-ray contrast giving parts of the prosthesis. That way it is possible to exactly control the position of these parts of the intervertebral disc prosthesis immediately after the implantation. Furthermore, it is possible to check if these parts have changed their position or if they are still in the right position in defined timely intervals.

Further useful measures are described in the dependent claims; the invention is described in the following by examples and figures.

DETAILED DESCRIPTION OF VARIOUS AND PREFERRED EMBODIMENTS

Figure 1A:
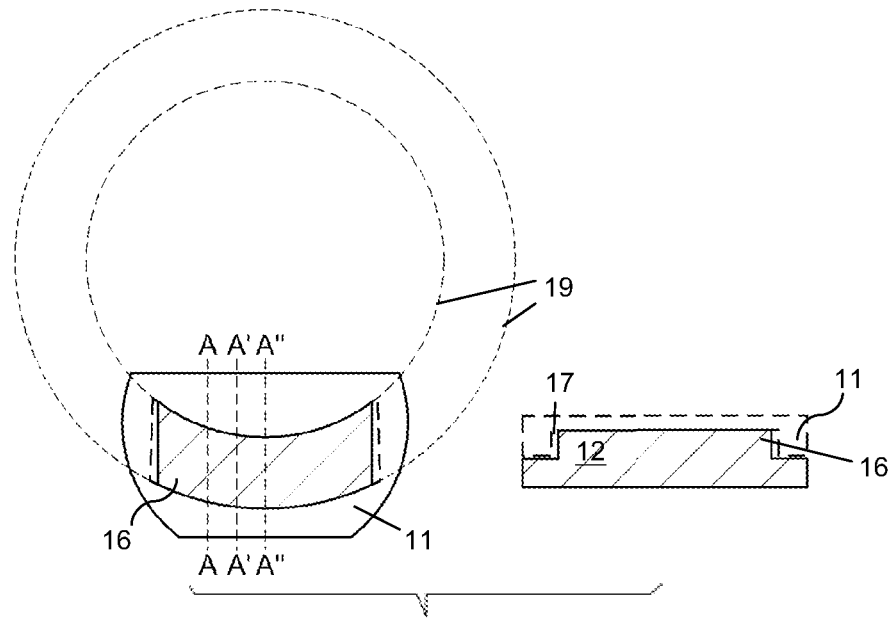
FIG. 1 a-c Schematic illustration of a median transverse section (left) and median frontal section (right) of a two-part intervertebral disc prosthesis, as per the invention, with ventrally curved, articulating convexity and concavity, which are laterally not rounded off (for the lumbar spine)
  a: schematic illustration of the sliding partners in a median position of the upper and lower sliding partner
  b: maximally anticlockwise moved upper sliding partner with concavity
  c: maximally clockwise moved upper sliding partner with concavity FIG. 2 a-c Schematic depiction of a median transverse section (left) and a median frontal section (right) of a two-part intervertebral disc prosthesis, as per the invention, with ventrally curved, each laterally rounded articulating convexity and concavity and dorsally displaced articulation area (for the lumbar spine)
  a: schematic depiction of the sliding partners in a median position of upper and lower sliding partner
  b: maximally anticlockwise moved upper sliding partner with concavity
  c: maximally clockwise moved upper sliding partner with concavity FIG. 3 Schematic depiction of sagittal sections in the planes A-A, A'-A', A"-A" as indicated in FIGS. 1a left and 2a left, of a two-part intervertebral disc prosthesis, as per the invention (for the lumbar spine) with
  Top: ventral gap-closure of the sliding partners
  Middle: dorsal gap-closure of the sliding partners
  Bottom: non-inclined sliding partners FIG. 4 a-c Schematic illustration of different shapes of the upper and lower sliding partners for the lumbar spine (a, b) and cervical spine (c)
Figure 1B:
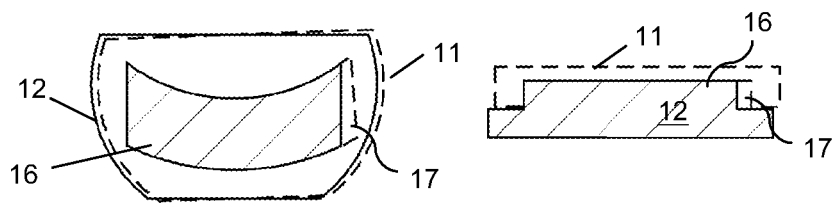
Figure 1C:
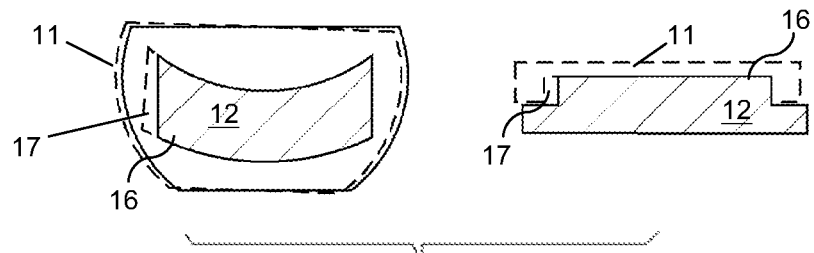

FIGS. 1 a-c and 2 a-c each show a transversal overview onto the sliding partners 11, 12 of a two-part intervertebral disc prosthesis, as per the invention, for the lumbar spine on the left, with curved articulating convexity 16 and concavity 17. A limited rotation of upper and lower sliding partner 11, 12, with respect to a fictitious vertical axis of the prosthesis, is possible due to the curved articulation areas. Convexity 16 and concavity 17 are displaced dorsally in the depicted models.

The ventral and dorsal curvature of the convexity 16 is derived from two circles with different radii but identical centers. The radii of curvature run in a constant distance towards each other. As per the invention, it is however intended that the secants can laterally run towards each other or diverge. The right parts of FIGS. 1 a-c and 2 a-c each schematically show a median frontal section of the prosthesis.

Figure 2A:
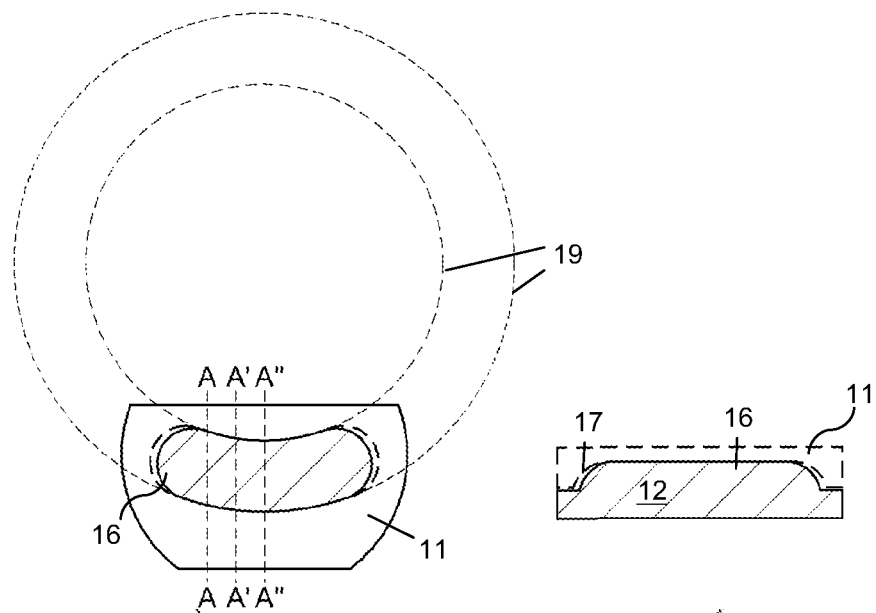
Figure 3:
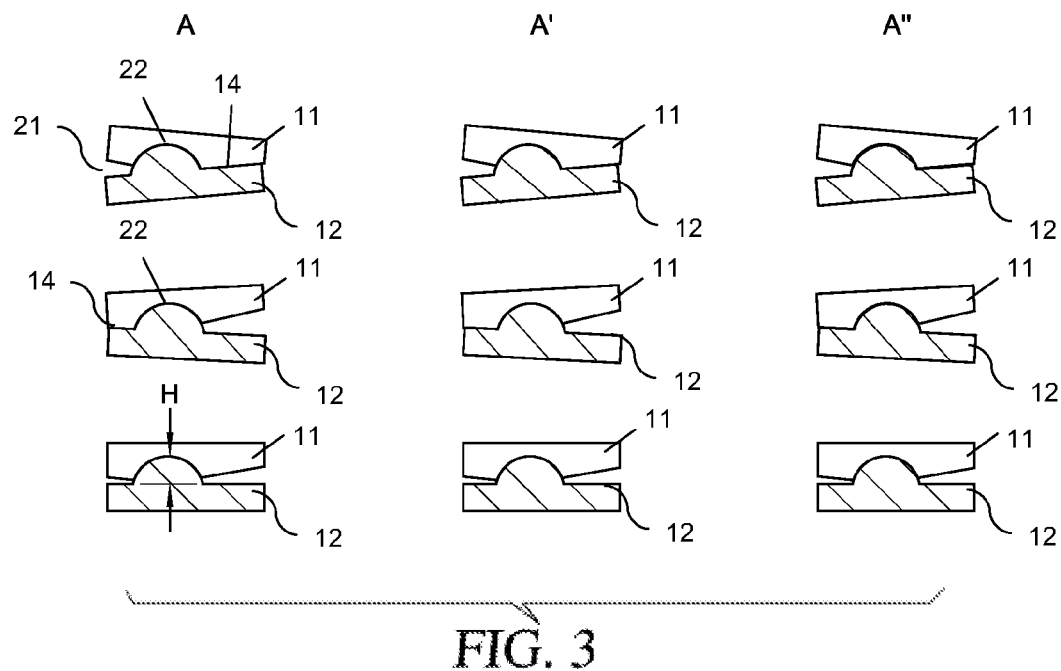

In FIGS. 1a and 2a the position of the three sections A-A, A'-A', and A"-A" are indicated, which are shown in FIG. 3.

In the left as well as in the right part of FIG. 1 a it can be well seen that in the case of not rotated sliding partners 11, 12, i.e. when the external circumferences of upper and lower sliding partner 11, 12 completely lie above each other in the transversal view, the concavity 17 of the upper sliding partner 11 is shaped a little broader to the left and right of the convexity 16, of the lower sliding partner 12 so that a "clearance" for the motion of the convexity 16, of the lower sliding partner 12 within the concavity 17 of the upper sliding partner 11 is given. The convexity 16 is centrally positioned within the concavity 17 in FIG. 1 a.

FIG. 1 b shows the position of the sliding partners 11, 12 of prosthesis, as per the invention, when the upper sliding partner 11, whose position is marked by the dotted line, is rotated fully in anticlockwise direction against the lower sliding partner 12. The rotation is limited by virtue of the contact. FIG. 1 c shows the position of the sliding partners towards each other when the upper sliding partner 11, is rotated maximally in clockwise direction. In each of the right part of FIGS. 1 b and c it can be well seen that the external circumferences of upper and lower sliding partner 11, 12 shift during maximal rotation. Upper and lower sliding partners 11, 12 are not in line with respect to their lateral external areas. In the case of an implanted intervertebral disc prosthesis, as per the invention, the rotation of the sliding partners 11, 12 towards each other depicts a rotation, with respect to a fictitious vertical axis, of the prosthesis.

Figure 2B:
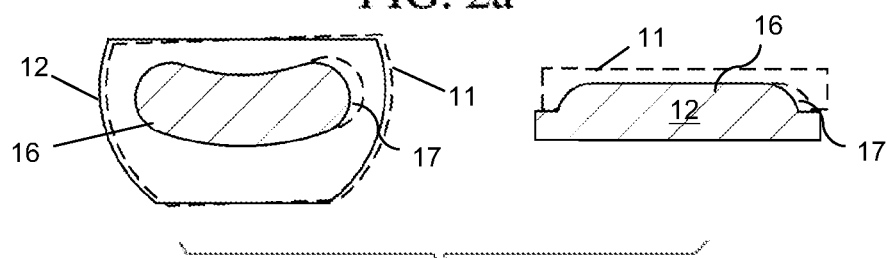
Figure 2C:
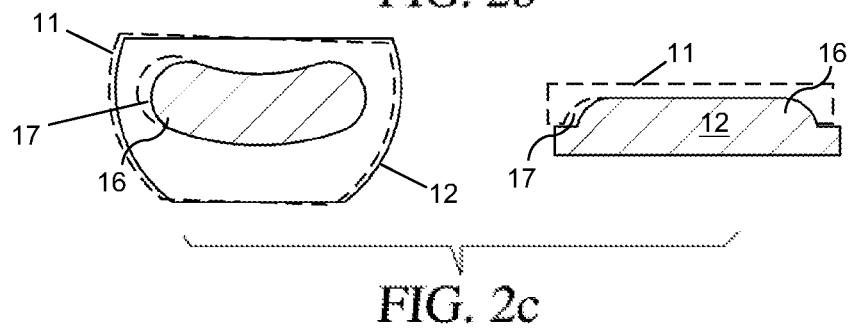

In FIGS. 1 a-c the surfaces of the convexity 16 and concavity 17 each terminate angularly. In FIGS. 2 a-c a design is depicted, as per the invention in which the lateral ends of the convexity 16 and concavity 17 are each rounded off.

FIG. 3 shows the sagittal sections of the sections A-A, A'-A', A"-A" for the lumbar spine, as indicated in FIGS. 1 a left and 2 a left. In each top section, a ventral gap-closure of the edges 14 of the sliding partners 11, 12 can be seen. By virtue of this, the aperture angle 21 of opposite sides of the convex-concave part of the articulation area 22 increases in size. In the middle section, a dorsal gap-closure can be seen and in each lower section, the sliding partners 11, 12 are not inclined towards each other. It can be well seen in all three sections how the position of the upper and lower sliding surface 22 are displaced from dorsal to ventral in the direction of the median section, i.e. from section A to A" as a result of the curvature in the transversal plane of the articulation areas.

Figure 4A:
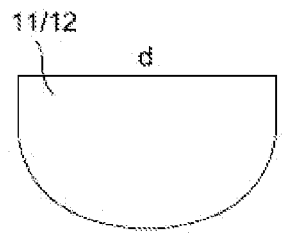
Figure 4B:
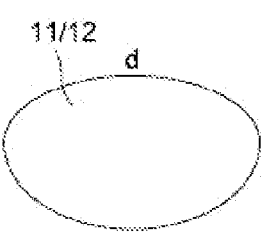
Figure 4C:
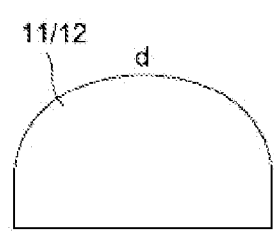

FIGS. 4 a-c each show an overview onto upper and lower sliding partner 11, 12, schematic alternative designs of the shape of the outer circumference. Hereby the small letters each mark the orientation with respect to the dorsoventral positioning of the plates for the lumbar spine (d=dorsal; v=ventral), which however, are vice versa for the cervical spine (v then dorsal and d then ventral).

Figures 5A, 5B:
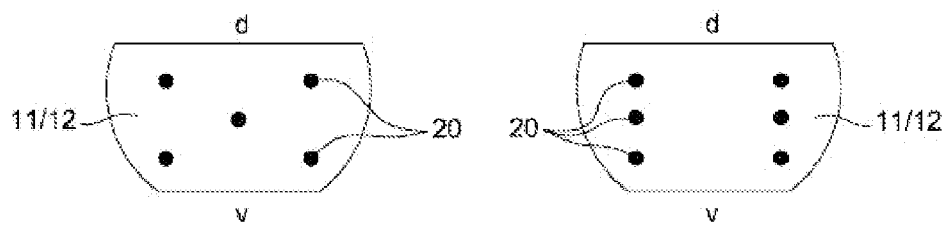
FIG. 5 a, b Schematic illustrations of the arrangement of anchoring teeth on the outsides of the upper and lower sliding partner for the lumbar spine FIG. 6 Schematic depiction of median frontal section of the two-part prosthesis with the outer surfaces of upper and lower sliding partner running non-parallel to one another.

In FIGS. 5a and 5b alternative arrangements for the anchoring teeth 20 on the outside of the upper and lower sliding partner 11, 12 for the lumbar spine are depicted. Again, the orientation of the sliding partners with respect to the dorsoventral orientation is indicated by the small letters (d=dorsal; v=ventral). Dorsally are in the middle no anchoring teeth 20 intended for sparing the vertebral bodies and facilitating implantation. The arrangement of the anchoring teeth allows for an implantation of the intervertebral disc prosthesis from ventral as well as from ventrolateral and lateral. For the cervical spine the reversed orientation applies, also without middle dorsal anchoring teeth 20.

The shown designs of a two-part intervertebral disc prosthesis, as per the invention, in the figures are only exemplary and not definite. Once given the above disclosure, many other features, modifications, and improvements will become apparent to the skilled artisan. Such other features, modifications, and improvements are therefore considered to be part of this invention.

Figure 6:
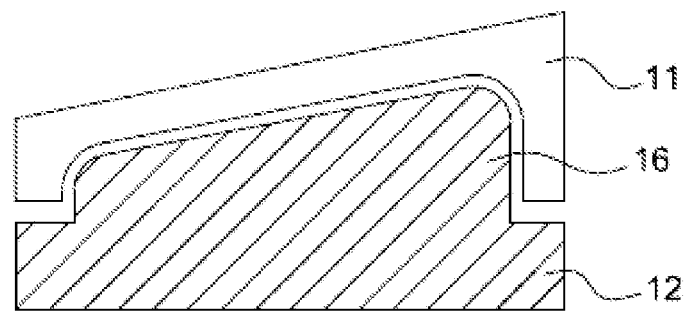

FIG. 6 shows a median frontal section of a prosthesis of the present disclosure with upper sliding partner 11 an lower sliding partner 12 with convexity 16. The outer surfaces of upper and lower sliding partner are not parallel.

Figure 7:
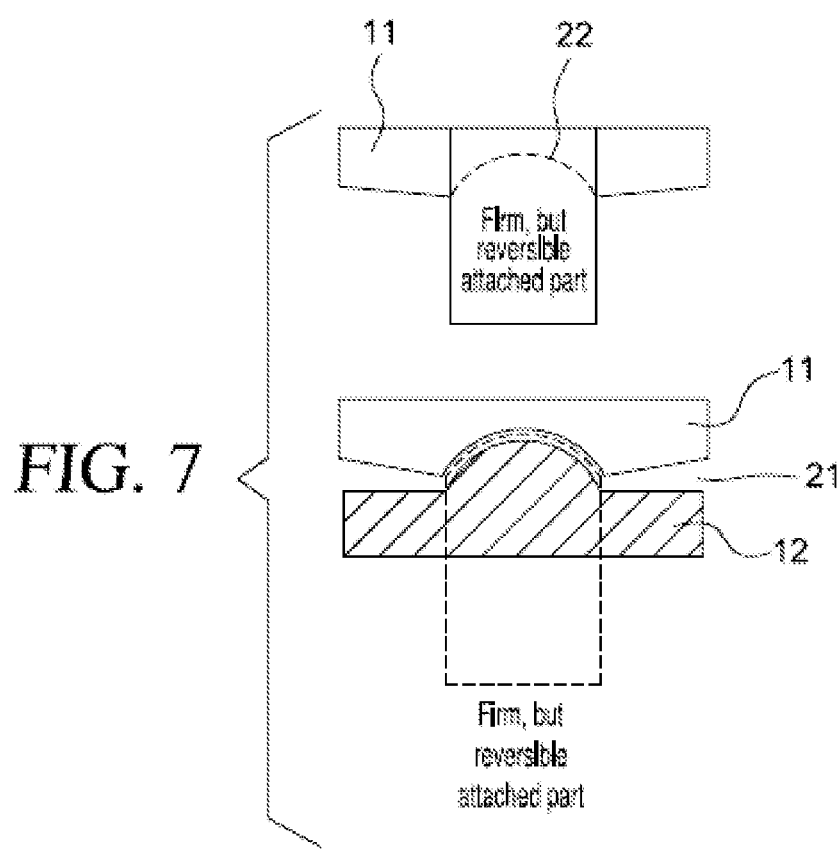
FIG. 7 Schematic representation of a firm, but reversible assembly.

FIG. 7 shows a schematic representation of a firm, but reversible assembly of upper or lower sliding partner 11, 12.

Figure 8A:
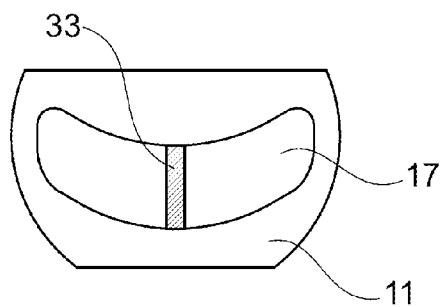
FIG. 8 Schematic representation of a bar in the concavity.
Figure 8B:
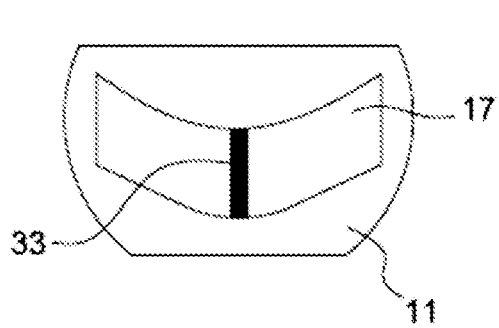

FIGS. 8 (a) and (b) show a schematic representation of an upper sliding partner 11 with a bar 33 in the concavity 17.

Figure 9:
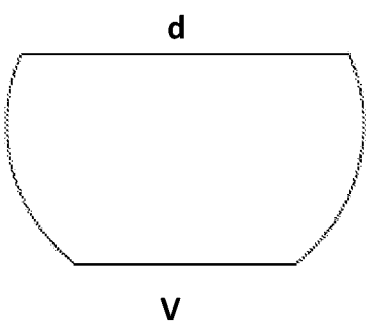
FIG. 9 Schematic illustration of the upper-sliding partner for the lumbar spine having ventrally tapering off radii.

FIG. 9 shows a schematic illustration of the upper-sliding partner for the cervical spine having dorsally tapering off radii. The small letters indicate dorsal (d) and ventral (v).

Figure 10:
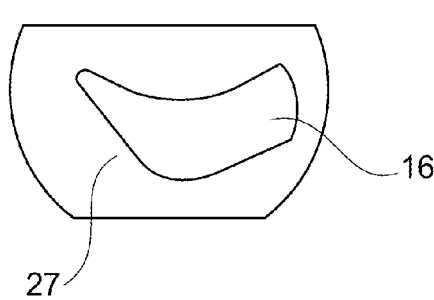
FIG. 10 Schematic illustration of a convexity with an asymmetrical ventrally arched curvature.

FIG. 10 shows a schematic illustration of a convexity with an asymmetrical ventrally arched curvature.

Figure 11:
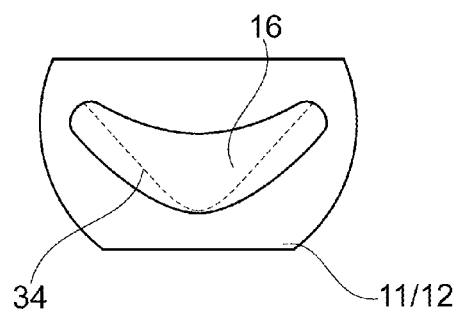
FIG. 11 Schematic depiction of the convexity having ventral and dorsal radii with a different curvature.

FIG. 11 shows a schematic depiction of the convexity having ventral and dorsal radii with a different curvature.

Figure 12:
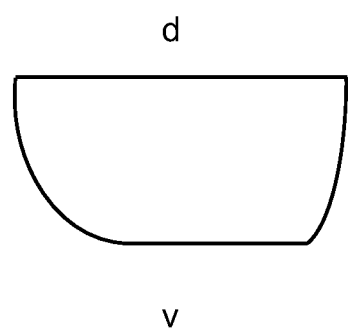
FIG. 12 Schematic depiction of an asymmetrically tapering off outer circumference of a sliding partner.

FIG. 12 shows a schematic depiction of asymmetrically tapering off outer circumference of a sliding partner.

REFERENCE NUMBERS 11 upper sliding partner
12 lower sliding partner
14 edge
16 convexity
17 concavity
19 circumference
20 anchoring teeth
21 aperture angle
22 articulation area
24 outer rim
25 gap closure
26 arched curvature
27 asymmetrical curvature
33 bar
34 dorsally/ventrally differing radii

REFERENCE LETTERS v ventral
d dorsal

The invention claimed is:

1. Intervertebral disc prosthesis for total replacement of an intervertebral disc within a lumbar and cervical spine, comprising a first sliding partner and a second sliding partner which are adapted to firmly assemble to either an upper or lower vertebral body and, wherein said first and second sliding partners articulate with each other via a sliding area located between the sliding partners, and wherein
   a) the first sliding partner has at a side opposite of a side for assembly with said upper or lower vertebral body a convexity, and the convexity correlates to a segment of a cylinder along its longitudinal axis laterally from right to left with a transversal ventrally directed arched curvature, wherein the convexity is surrounded dorsally, ventrally and laterally at both sides by an edge, and
   b) the second sliding partner has at an opposite side of the side for the assembly with the upper or lower vertebral body a concavity and the concavity corresponds to the convexity of the first sliding partner, wherein the concavity is surrounded dorsally, ventrally and laterally at both sides by an edge, and
   c) the edges of the first and second sliding partners have an outwardly opening aperture angle towards each other, wherein no inclination of the sliding partners towards each other is possible in a lateral direction, and a maximal possible motion of the sliding partners in dorsoventral direction is limited by a gap-closure of the edges of the first and second sliding partners, and
   d) the rotation of the first and second sliding partners towards each other is limited by a tolerance between the convexity and concavity laterally right and left of the sliding area.

2. Intervertebral disc prosthesis according to claim 1, wherein a greater inclination of the sliding partners towards each other is possible in a ventral direction than in a dorsal direction.

3. Intervertebral disc prosthesis according to claim 1, wherein a height of the cylindrical convexity is reduced conically on one side along a longitudinal axis and the edge is adapted to the reduction of the height.

4. Intervertebral disc prosthesis according to claim 1, wherein a ventral and dorsal radius of curvature of an outer circumferences of the curved convexity and corresponding concavity are equal or different in a transversal view.

5. Intervertebral prosthesis according to claim 1, wherein the maximal possible motion of the sliding partners is limited by
   a) the radius of curvature as well as a height of the convexity and a height of the concavity and the respective edges surrounding the sliding area ventrally and dorsally, and
   b) the aperture angle between the edges of the sliding partners, which is formed by the edges running at an incline and/or horizontally and a gap-closure during terminal contact of the edges of sliding partners, and
   c) the tolerances between the convexity and concavity laterally to the right and left and an extend of a curvature of the sliding area during rotation of the sliding partners, with respect to a fictitious vertical axis.

6. Intervertebral disc prosthesis according to claim 1, wherein the first and second sliding partner are built in one piece.

7. Intervertebral disc prosthesis according to claim 1, wherein the convexity of the first sliding partner is permanently or firmly, but reversibly attached to the first sliding partner, and/or the concavity of the second sliding partner is permanently or firmly, but reversibly attached to the second sliding partner.

8. Intervertebral disc prosthesis according to claim 1, wherein the sliding partners and/or parts of the sliding partners are made of the same material.

9. Intervertebral disc prosthesis according to claim 1, wherein the surfaces of the first and/or second sliding partner or parts of surfaces of the first and/or second sliding partner are coated equally.

10. Intervertebral disc prosthesis according to claim 8, wherein a tongue and groove assembly, a track and corresponding recess, a snap mechanism, gluing or screwing provides for a permanent or reversible assembly.

11. Intervertebral disc prosthesis according to claim 1, wherein a maximal height of the convexity is less than a semicylinder.

12. Intervertebral disc prosthesis according to claim 1, wherein a maximal aperture angle upon one-sided gap-closure via the edges of the first and second sliding partners during extension or flexion is between 6 and 10 degrees with a tolerance of an additional 3 degrees in dorsal and ventral direction.

13. Intervertebral disc prosthesis according to claim 1, wherein the ventrally directed arched curvature of the convexity and concavity of the first and second sliding partners slows down rotation around a fictitious vertical axis.

14. Intervertebral disc prosthesis according to claim 1, wherein the convexity and the respective corresponding concavity are dorsally displaced up to 4 mm away from a mediosagittal section.

15. Intervertebral disc prosthesis according to claim 1, wherein surface and shape of an outer circumference of the first and second sliding partner are equal and can thereby be adapted to the corresponding size of the vertebral body to which they are to be assembled.

16. Intervertebral disc prosthesis according to claim 1, wherein the first and/or second sliding partner are designed in such a way that in the frontal and/or sagittal view an outside and inside of the first and/or second sliding partners run parallel relative to one another.

17. Intervertebral disc prosthesis according to claim 1, wherein the transversal ventrally arched curvature of the convexity of the first sliding partner and concavity of the second sliding partner is in a transversal view symmetrical from central to both lateral sides.

18. Intervertebral disc prosthesis according to claim 17, wherein the convexity has a discontinuation in the middle and the corresponding concavity has a discontinuation in the form of a bar.

19. Intervertebral disc prosthesis according to claim 1, wherein the first and second sliding partners are plane or convex and coated bio-actively.

20. Intervertebral disc prosthesis according to claim 1, wherein the first and/or second sliding partner are configured to engage an instrument for implantation or explantation.

21. Intervertebral disc prosthesis according to claim 1, having in a frontal view a maximal breadth of 14 to 48 mm, in a sagittal view a maximal depth of 11 to 35 mm and a maximal height of 4 to 18 mm.

22. Intervertebral disc prosthesis according to claim 1, wherein the prosthesis is suitable for implantation into a lumbar spine, wherein an outer circumference of the first and second sliding partners tapers off ventrally in the transversal view.

23. Intervertebral disc prosthesis according to claim 1 suitable for implantation into a cervical spine, and wherein an outer circumference of the first and second sliding partners tapers off dorsally in the transversal view.

24. Intervertebral disc prosthesis according to claim 22, wherein the tapering off of the outer circumference of the first and second sliding partners, has laterally an identical or asymmetric curvature.

25. Intervertebral disc prosthesis according to claim 23, wherein the tapering off of the outer circumference of the first and second sliding partners, has laterally an identical or asymmetric curvature.

26. Intervertebral disc prosthesis according to claim 1, wherein non X-ray contrast giving parts are each marked under their surface with one or more radiolucent tags.

27. Intervertebral disc prosthesis according to claim 1, wherein the first and second sliding partners are blunt and have for their primary anchorage with vertebral bodies rows of anchoring teeth, that are either arranged from dorsal to ventral laterally straight or at an incline or ventral and dorsal in lateral alignment, wherein a respective dorsal row has only laterally arranged anchoring teeth.

28. Intervertebral disc prosthesis according to claim 1, wherein the sliding partners and/or parts of the sliding partners are made of different materials.

29. Intervertebral disc prosthesis according to claim 1, wherein the surfaces of the first and/or second sliding partner or parts of the surfaces of the first and/or second sliding partner are coated differently.

30. Intervertebral disc prosthesis according to claim 1, wherein surface and shape of an outer circumference of the upper and lower first and second sliding partners are different and can thereby be adapted to the corresponding size of the vertebral bodies to which they are to be assembled.

31. Intervertebral disc prosthesis according to claim 1, wherein the first and/or second sliding partner are designed in such a way that in the frontal and/or sagittal view an outside and inside of the first and/or second sliding partner run non parallel relative to one another.

32. Intervertebral disc prosthesis according to claim 1, wherein the transversal ventrally arched curvature of the convexity of the first sliding partner and concavity of the second sliding partner is in a transversal view asymmetrical from central to both lateral sides.

33. Intervertebral disc prosthesis according to claim 1, wherein the extent of the arched curvature allows a limited rotational motion between the sliding partners clock and counter-clockwise with respect to a fictitious vertical axis of up to 3 degrees for the lumbar spine, and up to 6 degrees for the cervical spine, with a tolerance of an additional 2 degrees clock and counter-click wise.

* * * * *